United States Patent
De La Torre-Bueno

(10) Patent No.: US 9,659,153 B2
(45) Date of Patent: May 23, 2017

(54) SYSTEM FOR TRACKING BIOLOGICAL SAMPLES

(75) Inventor: Jose De La Torre-Bueno, Encinitas, CA (US)

(73) Assignee: DAKO DENMARK A/S, Glostrup (DK)

(*) Notice: Subject to any disclaimer, the term of this patent is extended or adjusted under 35 U.S.C. 154(b) by 2804 days.

(21) Appl. No.: 11/642,253

(22) Filed: Dec. 19, 2006

(65) Prior Publication Data

US 2007/0122797 A1 May 31, 2007

Related U.S. Application Data

(62) Division of application No. 10/294,996, filed on Nov. 13, 2002, now Pat. No. 8,676,509.

(60) Provisional application No. 60/332,948, filed on Nov. 13, 2001.

(51) Int. Cl.
| | |
|---|---|
| G01N 33/48 | (2006.01) |
| G06F 19/00 | (2011.01) |
| G06F 19/24 | (2011.01) |
| G06Q 50/24 | (2012.01) |
| G06G 7/58 | (2006.01) |
| B01L 3/00 | (2006.01) |
| G01N 35/00 | (2006.01) |

(52) U.S. Cl.
CPC ............ *G06F 19/366* (2013.01); *G06F 19/24* (2013.01); *G06F 19/32* (2013.01); *G06Q 50/24* (2013.01); *B01L 3/545* (2013.01); *G01N 2035/00881* (2013.01); *G06F 19/322* (2013.01)

(58) Field of Classification Search
CPC ........... G06F 19/18; G06F 19/22; G06F 19/24
See application file for complete search history.

(56) References Cited

U.S. PATENT DOCUMENTS

| | | |
|---|---|---|
| 4,311,667 A | 1/1982 | Gocho |
| 4,967,606 A | 11/1990 | Wells et al. |
| 5,068,091 A | 11/1991 | Toya |
| 5,073,504 A | 12/1991 | Bogen |
| 5,289,385 A | 2/1994 | Grandone |
| 5,338,358 A | 8/1994 | Mizusawa et al. |
| 5,346,672 A | 9/1994 | Stapleton et al. |
| 5,355,439 A | 10/1994 | Bernstein et al. |
| 5,380,486 A | 1/1995 | Anami |
| 5,399,316 A | 3/1995 | Yamada |
| 5,416,029 A | 5/1995 | Miller et al. |
| 5,425,918 A | 6/1995 | Healey et al. |
| 5,439,649 A | 8/1995 | Tseung et al. |
| 5,552,087 A | 9/1996 | Zeheb et al. |
| 5,573,727 A | 11/1996 | Keefe |
| 5,578,452 A | 11/1996 | Shi et al. |
| 5,595,707 A | 1/1997 | Copeland et al. |
| 5,646,049 A | 7/1997 | Tayi |
| 5,650,327 A | 7/1997 | Copeland et al. |
| 5,654,199 A | 8/1997 | Copeland et al. |
| 5,654,200 A | 8/1997 | Copeland et al. |
| 5,696,887 A | 12/1997 | Bernstein et al. |
| 5,735,387 A | 4/1998 | Polaniec et al. |
| 5,839,091 A | 11/1998 | Rhett et al. |
| 5,896,488 A | 4/1999 | Jeong |
| 5,948,359 A | 9/1999 | Kalra et al. |
| 5,963,368 A | 10/1999 | Domanik et al. |
| 5,966,309 A | 10/1999 | O'Bryan et al. |
| 6,045,759 A | 4/2000 | Ford et al. |
| 6,080,363 A | 6/2000 | Takahashi et al. |
| 6,093,574 A | 7/2000 | Druyor-Sanchez et al. |
| 6,096,271 A | 8/2000 | Bogen et al. |
| 6,141,602 A | 10/2000 | Igarashi et al. |
| 6,151,535 A | 11/2000 | Ehlers |
| 6,215,894 B1 | 4/2001 | Zeleny et al. |
| 6,290,907 B1 | 9/2001 | Takahashi et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,374,989 B1 | 4/2002 | van Dyke, Jr. et al. |
| 6,403,036 B1 | 6/2002 | Rodgers et al. |
| 6,403,931 B1 | 6/2002 | Showalter et al. |
| 6,405,609 B1 | 6/2002 | Richards et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,520,313 B1 | 2/2003 | Kaarakainen et al. |
| 6,525,835 B1 * | 2/2003 | Gulati .......................... 358/1.18 |
| 6,534,008 B1 | 3/2003 | Angros |
| 6,544,798 B1 | 4/2003 | Christensen et al. |
| 6,582,962 B1 | 6/2003 | Richards et al. |
| 6,615,763 B2 | 9/2003 | Edwards et al. |
| 6,632,598 B1 | 10/2003 | Zhang et al. |
| 6,635,225 B1 | 10/2003 | Thiem et al. |
| 6,715,870 B2 | 4/2004 | Kiene et al. |
| 6,735,531 B2 | 5/2004 | Rhett et al. |
| 6,746,851 B1 | 6/2004 | Tseung et al. |
| 6,800,249 B2 | 10/2004 | De La Torre-Bueno |
| 6,821,072 B2 | 11/2004 | Thiem et al. |
| 6,855,292 B2 | 2/2005 | Angros |
| 6,855,559 B1 | 2/2005 | Christensen et al. |
| 6,890,759 B2 | 5/2005 | Bierre et al. |
| 6,951,663 B1 | 10/2005 | Edwards et al. |
| 7,135,992 B2 | 11/2006 | Karlsson et al. |
| 7,142,852 B2 | 11/2006 | Tell et al. |
| 7,184,610 B2 | 2/2007 | Weinstein et al. |
| 7,226,788 B2 | 6/2007 | De La Torre-Bueno |
| 7,303,725 B2 | 12/2007 | Reinhardt et al. |
| 7,378,055 B2 | 5/2008 | Lemme et al. |
| 7,396,508 B1 | 7/2008 | Richards et al. |
| 7,400,983 B2 | 7/2008 | Feingold et al. |
| 7,404,927 B2 | 7/2008 | Lemme et al. |
| 2003/0215936 A1 * | 11/2003 | Kallioniemi et al. ..... 435/287.1 |

FOREIGN PATENT DOCUMENTS

| | | |
|---|---|---|
| WO | WO 02/056121 | 7/2002 |
| WO | WO 2005/031312 | 4/2005 |

OTHER PUBLICATIONS

Juroshek et al., A High-Power Automatic Network Analyzer for Measuring the RF Power Absorbed by Biological Samples in a TEM Cell 1984, IEEE, gpo 818-824.

Meldrum et al., ACAPELLA, a capillary-based submicroliter automated sample preparation system for genome analysis, 1999, IEEE, p. 39-48.

Suckau et al., Automation of MALDI-TOF Analysis for Proteomics, 1999, IEEE, p. 1-5.

Garrett et al., Successful techniques for supporting multidisciplinary science programs with 'ROPOS: 1999, IEEE, p. 753-756.

* cited by examiner

*Primary Examiner* — Eric S Dejong

(57) ABSTRACT

Systems, methods, and apparatus are described for the handling of biological specimens for analysis. The systems, methods and apparatus are designed to reduce errors in misidentification, incorrect processing, and recordkeeping and reporting. The systems, methods, and apparatus can also provide real time tracking of samples at any stage, from collection to processing to analyzing to storage.

23 Claims, 2 Drawing Sheets

SYSTEM FOR TRACKING BIOLOGICAL SAMPLES

CROSS REFERENCE TO RELATED APPLICATIONS

This application is a Divisional application of and claims, under 35 U.S.C. §120, the benefit of priority to U.S. patent application Ser. No. 10/294,996, filed Nov. 13, 2003 now U.S. Pat. No. 8,676,509 which claims the benefit of priority under 35 U.S.C. §119(e) to U.S. Provisional Application No. 60/332,948, filed Nov. 13, 2001, the contents of each of which applications are incorporated by reference in their respective entirety for all purposes; this application is also related to a co-pending U.S. patent application Ser. No. 11/641,246, titled "A System For Tracking Biological Samples", filed on Dec. 19, 2006.

TECHNICAL FIELD

This invention relates to the field of laboratory science and more particularly to the systems, methods and apparatus that can be used in the laboratory.

BACKGROUND

Advances in science have made it possible to extract a wide variety of information about an individual from a biological sample obtained from that individual. For example, it can assess the health, identify possible future health issues, and provide the genetic makeup of the individual. The results of any analysis, however, loose much of their beneficial qualities when the analysis is attributed to the wrong individual or if the sample is processed incorrectly.

Much, if not all, of these analyses are processed in laboratories. The laboratory usually obtains its samples from institutions, such as the hospital, clinic, or police, and from individuals, such as samples sent to it from individuals using, for example, a Home HIV test kit. In these laboratories, many samples are processed daily where they may pass through many sets of hands and potentially be subjected to many different tests. Each time a sample is handled, there is the potential for an error to occur. In many cases, a human operator is the source of the error. For example, in the collection of the sample, the sample should be clearly identified, e.g., from whom the sample was obtained. Samples, however, once removed from their natural environment, such as an individual's person, tend to look very similar to other samples of like kind. Because of this, mix-ups have been known to happen when the information was incorrectly transcribed, labels were placed on the wrong samples, or the identifying information was inadvertently omitted or was incomplete. Moreover, errors can occur in the processing steps as well, such as the wrong reagents being used or the wrong tests being performed. It is, therefore, desirable that laboratories implement systems, methods, and apparatus for maintaining the fidelity of their work, i.e., the proper analysis on the right sample and being able to report the same to the person who ordered the test.

To prevent errors of this kind, elaborate and costly systems of paperwork are used. Current systems may also use barcodes to identify the samples, such as patient information, as well as barcodes to carry other information, such as instructions about tests to be run. Often, this leads to a need to use multiple barcodes, each directing a specific function or holding information related to the sample. Because of the limited space available for these barcodes on sample containers or of the risk of confusion, one barcode may need to be placed over another in order to run the slide on more than one test. Alternatively, the old barcodes can be removed; however, it must be done without removing the barcode holding needed information, such as the patient information. Moreover, since most barcodes look similar, the more widespread the use of barcodes for each specific task or bit of information, the greater the likelihood of placing the wrong barcode on a sample, possibly misidentifying the sample and/or providing incorrect instructions for handling the sample.

Once a sample is collected, it is labeled, or otherwise identified, and sent to a laboratory for further processing. For example, in a hospital setting, a health care provider will collect samples from a patient. These samples might be biopsies (pieces of tissue removed surgically) or other samples from a person including samples of blood, urine, stool, scrapings from the skin, or any other location, hair etc. Typically one or more samples are bagged, labeled and sent to a laboratory with a work order that specifies what diagnostic tests are to be performed on them. The laboratory may be in the same building as where the sample was collected or it may be in another facility or even in another country. The laboratory may even forward the sample or a portion of the sample to yet another laboratory to do tests it cannot perform.

Once the sample arrives at the laboratory to be processed, the sample is prepared for analysis. For example, the sample can be taken to a grossing station. At the grossing station, the sample is removed from its container and the desirable portions of the sample can be extracted and placed in the appropriate setting for further processing. For example, the portions can go into small baskets called cassettes, which are used to carry the samples while they are fixed and embedded in wax. Once embedded, the samples can be sliced on a microtome and placed on slides. Since the slices are very thin (microns) many slides can potentially be made from one cassette. While slides are described, other receptacles for holding the sample are used in the laboratory, and they are contemplated for use herein, for example, tubes, cuvettes, biochips, and microplates, to name just a few. In each case, the source of the extracted portions of the sample must be correctly identified.

From here, the slides with the sample may go on to be specifically treated for the test to be run on it, such as staining with reagents. The types of reagents used will depend upon the test that is to be performed. Slides can be stained with a variety of chemicals that will make relevant cells, germs or other structures visible. Once the slides are processed, they can be read by an automated microscope, such as an ACIS (Automated Cell Image System) or by an individual through a microscope. A pathologist can examine the slide or the image of the slide and issue a diagnostic report that can be sent back to the clinician. Throughout this process, the user should ensure that all the slides are identified properly and that the proper test is being performed.

A fluid sample can be processed in a similar manner except that, instead of the grossing and microtome steps, the cells in the sample can be spun down with a centrifuge and transferred to a slide. Smears may be applied directly to a slide by hand. There are a number of other patented and non-patented methods of getting cells onto a slide that could be used in conjunction with the system described herein.

SUMMARY

In one general aspect, the invention contemplates a laboratory or a network of laboratories equipped with readers (scanners) such as barcode readers, magnetic strip readers, keyboards, or a similar device that can "input" data directly or indirectly into a computer or computer system, such as Optical Character Recognition (OCR) readers. It is envisioned that these scanners can be located at desired area in the laboratory or throughout the facility, e.g., at one or more of the following areas, including but not limited to, the grossing stations, microtome, reagent dispensing stations, automated cell image analysis stations, or storage areas.

In another general aspect, the samples are assigned a unique identifier composed of numbers, letters, and/or symbols. The identifier can be in human readable text and/or computer readable text. In one embodiment, the identifier is a universal unique identifier (UUID). These identifiers are unique across both space and time. Use of UUIDs does not require a registration authority for each identifier; instead, it uses a unique value over space for each UUID generator. Methods and algorithms for generating unique identifiers are known in the art, for example, UUIDLib is a Macintosh shared library that generates UUID identifiers. Global unique identifiers (GUID) are used by Microsoft to identify anything related to its system. One source of information about unique identifiers is the world wide web. The unique identifier can be read by a human and/or by a computer (e.g., scanners). In other embodiments, the identifiers are generated from one source that dispenses identifiers sequentially. In still other embodiments, algorithms used in computers generate a unique 128 bit number. Other methods of generating a unique identifier are known to those skilled in the art.

Once assigned, the unique identifier remains associated with the particular sample. Other samples derived from the original sample, such as when the sample is being processed at the grossing station, are assigned their own unique identifier. In one embodiment, the unique identifier is merely an identifier. In another embodiment, the unique identifier can also provide information about the identifier, such as the location of where and/or when the identifier was assigned, based upon a characteristic of the identifier. For example, identifiers that begin with 01 can be designated to have originated from a particular facility. In certain embodiments, the identifier does not hold any information pertaining to the sample. In other words, the identifier does not hold any information about the source of the sample, the tests to be run on it, or what other samples may be related to it. The unique identifier can be read by scanners or otherwise inputted into a computer, such as by hand. Once in the computer, the information can be transmitted to a database.

In another general aspect, a central database can be utilized to house all the information associated with the sample. The central database can store any and all information about the sample, source information, the tests to be performed, the results obtained from the tests, and the location of the sample, to name just a few examples of the type of information. The data in the central database can be updated each time new information is received. In certain embodiments, the central database receives and stores information about the sample, such as the name of the patient (source) and other identifying information, type of sample, when collected, and who collected it. The central database can also receive and store information about what tests are to be performed. It can also receive and store information about when it was checked into the lab. The central database can also receive and store information about how the sample was processed, what reagents were used and when it was done, and whether there are other samples prepared from the original sample and information relating to them, or otherwise linking the data about the original sample and the data from all samples derived from it. The central database can receive and store the results of the tests. The central database can also receive and store information about additional tests to be run or changes to existing orders. The central database can also allow approved users to access this information. In certain embodiments, the data can be accessed from a terminal in close proximity to the laboratory or the database, or from a remote location, over the LAN, WAN, VPN or the world wide web.

In another general aspect, the central database may be in communication with the readers or scanners for inputting the unique identifies, such as the barcode readers. The central database may be in communication with the equipment in the laboratory, such as the microtome, centrifuge, reagent dispensers, and automatic image analyzer, to name just a few pieces of equipment found in laboratories. The readers or scanners may also be in communication with the equipment, so that all three, scanners, equipment, and the central database are in communication with each other.

In another general aspect, the invention contemplates a computer system including a database having records to the identity of a biological sample collected from a subject and the identity of a diagnostic analysis to be performed on the biological sample and a remote user interface, such as readers, scanners, display screens, printers and computer terminals, capable of receiving and/or sending the records, for use in matching the biological sample with the diagnostic analysis to be performed on the biological sample.

In another general aspect, the invention contemplates a computer-assisted method for processing a biological sample including: using a programmed computer including a processor, an input device, and an output device, including inputting into the programmed computer, through the input device (readers, scanners, mouse, keyboard), data including the identity of a biological sample collected from a subject and the identity of a diagnostic analysis to be performed on the biological sample; determining, using the processor, the parameters of the diagnostic analysis; and outputting, to the output device, display screens or printers, the results of the diagnostic analysis.

In another general aspect, the invention includes methods for the automated analysis of a biological sample, including the steps of: providing a user with a mechanism for electronically communicating the identity of a biological sample collected from a subject and the identity of a diagnostic analysis to be performed on the biological sample; providing the biological sample with a unique identifier; providing the diagnostic analysis with a unique identifier; optionally providing the user with an opportunity to communicate a desired modification to the diagnostic analysis; allowing the user to transmit any of the above identified information to a server; allowing a second user to obtain the information from the server; correlating the information with the biological sample; performing the diagnostic analysis on the biological sample; and inputting into a programmed computer, through an input device, data including the results of the diagnostic analysis.

In another general aspect, the invention contemplates methods of selecting a therapy for the patient based upon: obtaining a patient sample from a caregiver; identifying a diagnostic profile to be performed on the sample; providing a caregiver with a mechanism for electronically communicating the identity of the biological sample collected from the patient and the identity of the diagnostic profile to be performed on the biological sample to a server, wherein the patient and profile are given a unique identifier; and allowing a second user to obtain the information from the server. A diagnostic profile may include a series of tests to be run on a particular sample.

In another general aspect, equipment useful for the system can include a grossing station that can read the barcode, or otherwise input the identifier into the system. For example, a scanner reads the barcode on a sample bag and a list of tests to be done on the sample, to provide guidance to the pathologist doing the grossing, is displayed on a screen. It may also be able to print out the barcodes for the appropriate number of cassettes, sample tubes, or other sample holders. If the cassettes and tubes are prelabled with a barcode, the pathologist can scan the labels to associate the barcodes with the cassettes or tubes of samples. This method allows for the automatic entry of information to the database to maintain the linkage between the patient and sample and the intermediate sample carriers (cassettes and tubes).

Other equipment includes a microtome with a scanner that can read a barcode or other identifying mark. The scanner can read the barcode on the cassette or tube (i.e., the block of sample) and allow the database to transmit to the pathologist or technician information about what tests are to be performed on this block of sample and/or how many slides are to be prepared from the block of sample. It can then print out the required number of barcodes for each of the slides to be prepared. An autostainer and an automated microscope that can read the identifier and extract information from the database as well as transmit information to the database are contemplated as well.

The scanner, or similar device to input the identifier, such as a barcode reader, can be a component separate from the laboratory equipment or it can be integrated into the laboratory equipment. Even if the scanner is a component separate from the equipment, it may still be in communication with the equipment.

In still another aspect, a sample is assigned a unique identifier. In one embodiment, the unique identifier is in the form of a barcode. Information related to the sample is received by the central database and associated with the unique identifier. The sample is sent to the laboratory for processing. The laboratory is equipped with scanners for inputting the unique identifier, in this case barcode readers. At the laboratory, the user may scan the barcode of the sample to log in when the sample arrived in the laboratory. This information is received and stored by the central database. The user may take the sample to the grossing station. At the grossing station, the user may scan the barcode into a barcode reader. The unique identifier is received by the central database and it is noted that the sample is at the grossing station at a particular time. The database may also transmit to the user, for example on a display panel at the grossing station, information about how the sample is to be prepared.

The sample may then arrive at the microtome. The identifier of the sample is scanned, and the time and location is received by the central database. The central database can then transmit more information about processing the sample. For example, an order in the central database may state that five different slides of the sample are to be prepared from the original sample. There is, of course, no limitation on the number of slides that can be prepared. The central database may transmit this information to the user at the grossing station and may even automatically print out labels with unique identifiers to affix to each of the five slides with the biological sample, or the system may utilize another means of affixing the unique identifier to the slide, such as by encoding it by laser, stamping it, or encoded magnetic strip.

Alternatively, the user may place the samples on slides already assigned a unique identifier. The central database stores information about the new samples (e.g., that the samples associated with the new five identifiers are derived from the original sample, when they were prepared, and other useful information). This recordkeeping can be done with very little input from the user.

The slides can now be prepared for their specific test. The central database stores the information about how the sample is to be prepared and what tests are to be run on them. At each station, e.g., sample fixer, reagent dispenser, or analyzer, the sample can be scanned. This would log in the sample providing information such as location and time to be stored in the central database. It can also ensure that the slide is being processed properly. For example, if the sample is at the wrong station, there might be a display indicting such, the station may refuse to process the slide, and/or the information is logged so that one looking at the history of the slide would know where the error occurred. All this can be recorded without the need for the user to take any notes.

Once the slide is processed and the test results transmitted to the central database, the slides may then be put aside for storage. At the storage area, the user can scan the slide to log it in, providing a time and location for the slide in the central database, and set it aside. If a loose slide is found, the unique identifier can be scanned into the system to allow the central database to transmit the identifying information back to the user, as well as logging in the information of when and where the slide was found by noting which scanner read the barcode and when it happened. Use of unique identifiers as described herein allows for real time tracking as well as a convenient way to create a complete history of the slide with minimal input from a user. It is further contemplated that a network of laboratories can be similarly equipped so that samples can be shared easily and effectively.

The invention may further include one or more of the following embodiments. The unique identifier can be assigned at the moment the sample is removed from the patient's person. The unique identifier may be assigned when the sample reaches the laboratory. It is further contemplated that scanners may be found throughout the facility, in areas not associated with equipment in the laboratory, such as a user's desk. In addition, while slides are the subject of this example, they are only one example of the types of devices that can be used in the examination of biological samples. Any device used to process biological samples, such as tubes, cuvettes, vials, cassettes, biochips, and microplates, are also contemplated in the practice of the invention. Moreover, a user can be assigned an identifier. She can scan in her identification when the sample is scanned so that the central database can record not only when and where the sample was scanned, but also who scanned it in.

In another general aspect, the invention contemplates labels designed to hold information used in a laboratory equipped with scanners or other devices for inputting data into the system. The information may be patient information and/or information concerning the tests to be run. The presence of the scanners reduces the need for a user to record the data, as well as providing an efficient way to track the slides.

The details of one or more embodiments of the invention are set forth in the accompanying drawings and the description below. Other features, objects, and advantages of the invention will be apparent from the description, drawings, and the claims.

DESCRIPTION OF DRAWINGS

Like reference symbols in the various drawings indicate like elements.

DETAILED DESCRIPTION

Figure 1:
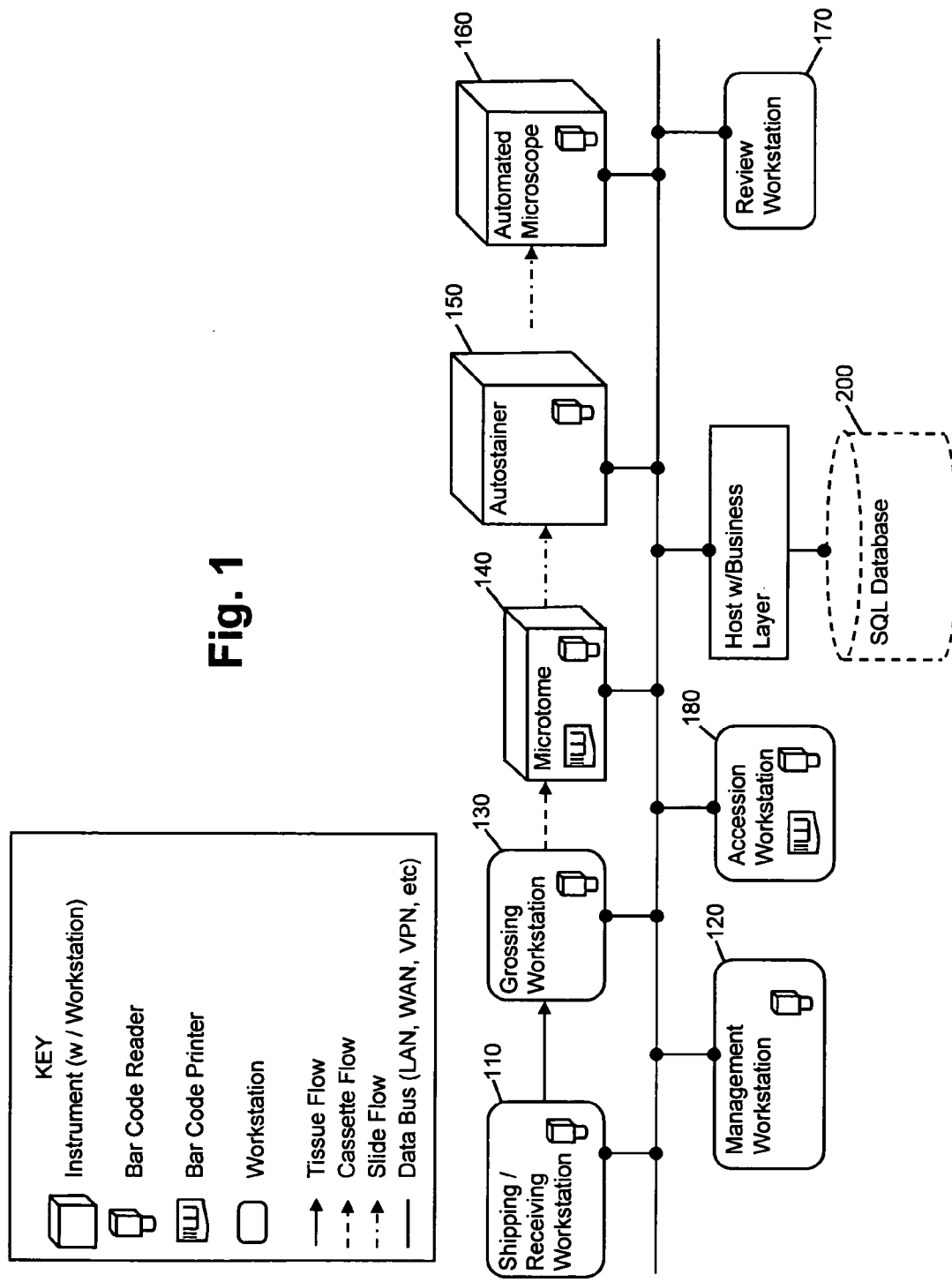
FIG. 1 is a diagram of an exemplary organization of one embodiment of the invention.

In one aspect, a system for tracking the relevant samples and information is provided. It is designed to work for a single laboratory or for a network of laboratories and clients. In other aspects, the methods and apparatus for tracking samples and information are also provided. FIG. 1 shows one example of the flow of samples and information.

In this example, the identifier is a printed barcode number and the sample is a tissue to be analyzed under a microscope.

1) A sample bag is received at laboratory receiving 110. The sender may have already used an accession workstation 180, to enter information into the central database 200 about the sample, such as information about the source of the sample, patient information, the tests required, and the barcode number of the bag and each sample container. The accession workstation 180 can be local or it can be at a remote location, such as in the surgery room where the sample may have been collected. Inputting information can also be done at the management workstation 120. The management workstation 120 can also allow configuration of all the instruments, as well as the laboratory information system (LIS), provide additional information or update information already in the system, and direct the processing of the sample.

2) A receiving clerk reads the bag barcode into the system. The clerk may also read the barcode on the package. This information could be linked to the delivery service so that the receipt of the package is automatically acknowledged to the delivery service. The central database finds the record of the shipment and displays a list of the expected contents for the clerk to check. If the individual samples do not have their own barcodes, the workstation can print them (as well as record the numbers).

3) At the grossing station 130, the technician shows the sample barcodes to the barcode reader and a screen displays a list of how the samples are to be divided for the requested tests. Note that no paper documentation needs to follow the sample because from the sample's unique identifier, the database can send, receive, and store the needed information. The sample may be subdivided into the needed number of vials or cassettes, as the case may be. If these vials or cassettes are prelabeled with unique barcodes, the operator shows them to the reader when he is finished to note that they are in use, otherwise the system assigns unique identifies to be affixed to the vial or cassettes. The unique identifiers can be affixed in any way known in the art, such as by affixing a label to the slide or imprinting it into the slide.

4) At the microtome 140, the same process is repeated, the operator shows the barcode of the cassette to the reader and a list appears of how many samples need to be cut for placement onto slides. Again, if the slides are not prelabeled, the station prints out the barcodes for the slides.

5) The labeled slides are loaded into an autostainer 150, which reads the barcodes and checks the central database to see what stains need to be applied to each slide.

6) Next, the slides are loaded in the automated microscope 160, which reads the barcode to see what magnification and other parameters to use to scan the slide. Automated microscopes include ACIS (automated cell image system) a device that scans the slides and presents images to the pathologist along with image processing tools to help in the diagnostic process. Apparatus for the automated analysis of samples are known in the art, for example, they are described in U.S. Pat. Nos. 6,215,892; 6,330,349; 6,418,236, the contents of which are incorporated by reference in their entirety.

7) Finally, an image is displayed to a pathologist who uses the image processing features of the review workstation 170 to study the image and arrive at a diagnosis.

These diagnostic quality review workstations 170 display the images captured by the image acquisition system. In order to assist the pathologist in interpreting a medical image, a view station may be able to perform a variety of image processing operations on the medical image. For example, the pathologist at the view stations may invoke algorithms to perform densitometry on selected regions of the medical image in order to identify concentration of a particular analyte within the tissue sample. Other image processing operations are useful for finding objects within the image such as the nuclei of the cells, computing an integrated optical density for the nuclei of the cells and reporting the number of molecules per cell. Most image processing operations output a fixed number (score), often falling within a predetermined range. Demographic data about the patient, which was irrelevant to the processing of the slide, might be fetched from the central database and displayed at this point.

Due to the size of some medical images for a single tissue sample, typically remote viewing is unworkable if there are bandwidth constraints. Compression algorithms can produce an image suitable for transmission, but the data lost during compression can lead to inaccurate results from the image analysis operations.

A system can be utilized in which a remote review workstation 170 is communicatively coupled to an image server and receives a compressed version of a source medical image. The remote review workstation 170 can uncompress and display the received medical image. The compressed medical image can be transmitted over a global packet-switched network such as the Internet. The remote review workstation 170 can select a region of the displayed medical image as a function of input received from a user. Based on the input, the remote review workstation 170 can transmit region information, such as a series of pixel coordinates, back to the image server. The image server can then apply image analysis operations to a region of the source medical image that corresponds to the selected region of the compressed medical image. In this manner, the data loss that occurs during image compression does not affect the image analysis operations. As such, the image analysis operations can produce more accurate results than if the operations were applied by the remote review workstation 170 on the compressed image. U.S. patent application Ser. No. 09/542, 091, filed Apr. 3, 2000, the contents of which are incorporated by reference, describes a system in which images are viewed at a site remote from the location of the ACIS microscope that collects the images. It further describes a method for carrying out the image processing at a remote site that has uncompressed versions of the images while transmitting compressed images for human viewing. Other means for viewing large images electronically are known to the skilled artisan. Therefore, in situations where the review workstation 170 is connected to the system with a limited bandwidth, e.g., over the WAN, one method for transmitting data involves generating a compressed medical image, transmitting the compressed medical image to a remote view station for display, selecting a region of the displayed medical image, and applying image analysis operations to a region of the source medical image corresponding to the selected region of the compressed medical imaged. The image displayed for review might be compressed, but the user's requests for image processing or scoring algorithms might be sent back to the central database for execution on uncompressed images. However, if there is no need to review the images from a remote location, e.g., over the LAN, then there is no reason not to send an uncompressed image.

An optional feature of the system can include users being assigned their own identifying string, such as a barcoded badge. They can then log onto any one of the stations by scanning their barcoded badge. One method of utilizing the feature is to have the user log onto the station when they log in a slide. The system can then provide information about who has handled the slide at any given stage of its processing. This system can also be used to assess the quality and quantity of work being handled by an individual.

Still other features of the system can include apparatus adapted for use in the system. For example, an autostainer may be designed to use its barcode reader to read IDs on the bottles of reagent to track which slides are stained with which lot of reagent. A scanner, such as a barcode reader, on a refrigerator or other sample storage space can be used to check in or check out samples for tracking purposes. An undedicated reader, for instance at a supervisor's station, could be used to identify a loose slide. It is contemplated that other equipment generally found in laboratories, not herein described, can also be adapted to transmit information to and/or receive information from the database to track and provide information about the sample or the process it undergoes.

The system takes advantage of being able to assign unique identifiers, and utilize scanners that read them, to faithfully transmit the information to a database. Each time a slide or sample passes through some station, the database can record this event. It is, therefore, possible to provide more detailed reports and tracking information with less effort then can be done with paper based systems. For instance, if a slide is missing, the database can provide information about which station it was last logged in, when it was logged in and who logged it in, without a user having written any of this information into the system. If a batch of reagent becomes suspect, the database can provide information about all the samples that used the reagent and the test results from that use. If a stat (rush) result is needed on a sample, the database can provide in real time information about where the sample is in the process.

The system may utilize a centralized database. One of the benefits of using a centralized database is that it does not matter if some steps in the processing of the sample occur at one facility and some at another. Since all the information is being stored in one database, someone accessing the database will see only the seamless processing of the sample. Furthermore, if a sample is sent from one facility to another, no paperwork need accompany it as long as the sample has its unique identifier. When the sample arrives at the new facility, its unique identifier can be scanned to log it in, to indicate its new location and when it arrived.

Figure 2:
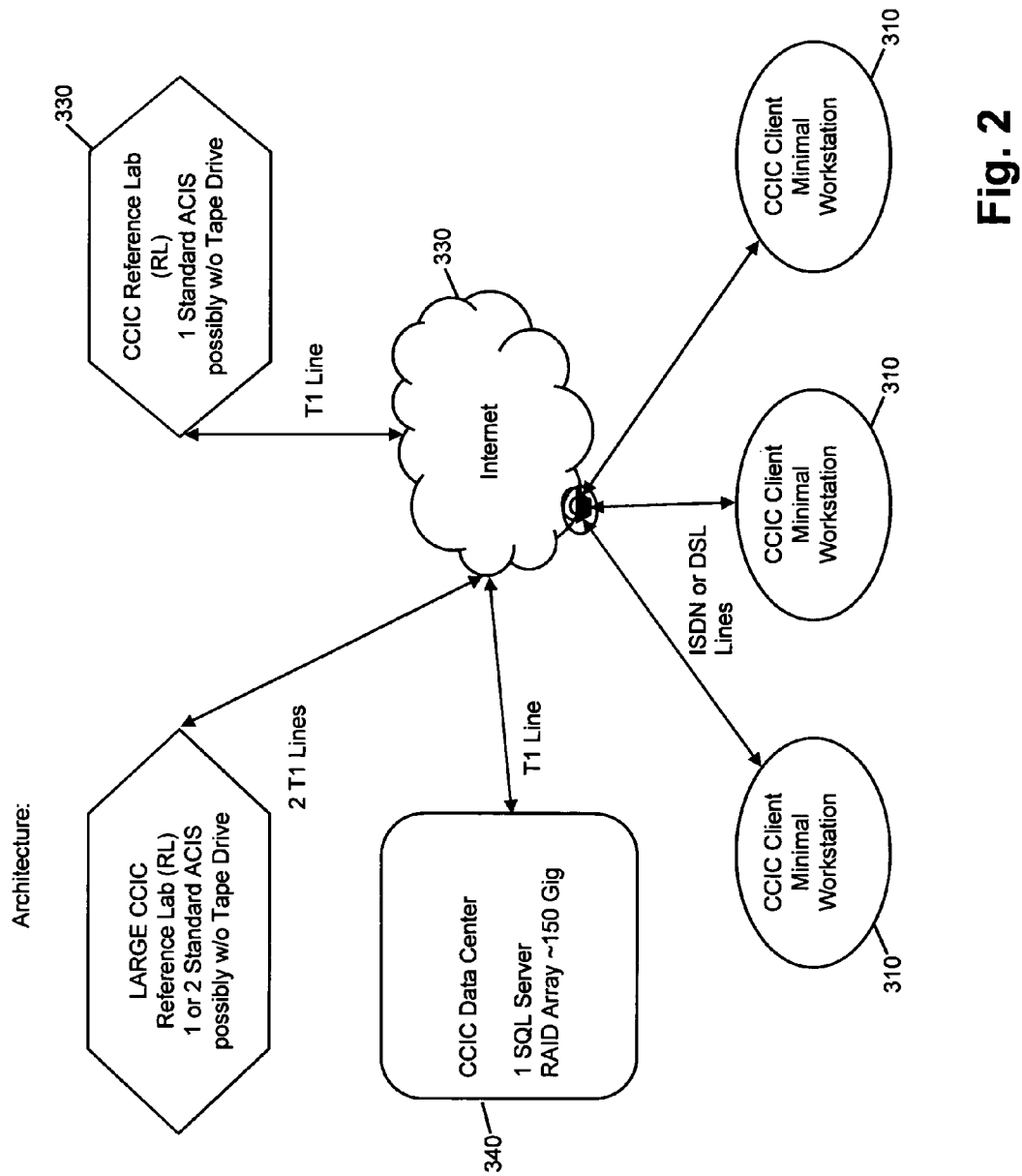
FIG. 2 is a diagram of an exemplary architecture of one embodiment of the invention.

FIG. 2 shows a block diagram of a system in which clients (who have review and accessioning workstations 310) are sending samples to reference laboratories 320 who are preparing slides and running them on an automated cell image system (ACIS). All of them are connected via the global Internet 330 to a data center 340, which is storing all the information. Table 1 shows an exemplary division of work in the application of an exemplary system.

TABLE 1

| Manual Event | Automatic Event |
|---|---|
| Sequence of Operation: For each Slide: | |
| Client enters accessioning info | DC captures accessioning information |
| | DC sends accessioning info to RL |
| Client sends samples | DC center captures shipping |
| | DC notifies RL to expect shipment |
| RL receives shipment | DC captures receiving information |
| RL prepares slides | |
| RL scans slides on ACIS | RL ACIS sends lossless compressed images to DC |
| | RL ACIS deletes images |
| | DC sends lossy compressed images to client |
| | DC notifies Client slides are ready for review |
| Client uses review analysis program to view slides and select regions | CW sends region coordinates to DC |
| | DC scores regions and sends scores back to CW |
| Client releases cases | CW prints report |
| | DC enters billing data in database |
| | DC archives images if archive fee paid then deletes from hard disk |
| At any time: | |
| Client requests case status on display on Client workstation | status CW queries DC and displays results [if the RL had barcode readers at grossing and sectioning, the display could indicate the exact stage of each slide] |
| Client requests re-review of archived case (if they have this service) | CW queries DC on availability of CW informs client how long tape mount will take |
| DC operator mounts tape | DC sends notification to Client |
| Client reviews case | |

RL = CCIC reference lab 320
Client = CCIC client
CW = Client's workstation 3 10
DC = CCIC data center 340

Although barcodes are referred to here, any globally unique system of identifiers could be used, for instance letters and numbers if Optical Character Recognition (OCR) readers were used. An OCR system that can distinguish 80 symbols can detect 10 quintillion (a billion billion) different 10-character labels.

In the system, each label is unique and is used to identify the information sent to the database and/or retrieved from the database. This allows any part of the system (within one laboratory or in other facilities) to work on the samples or slides without having to re-label for use with different equipment or for different processing steps.

Other components of the system may include an autostainer and an automated microscope that reads the same barcode and each extracts the information it needs from the database; a microtome with a barcode reader and printer, which can read the barcode on a cassette (block), look up in the database what tests are to be performed on slides cut from this block, and then print the required number of slide barcodes; and/or a grossing station that can read the barcode on a sample bag and display a list of tests to be done on this sample for the guidance of the pathologist doing the grossing. It would then either print the needed barcodes for the appropriate number of cassettes or sample tubes or otherwise encode the cassettes or samples. If they were prelabled it would read the labels. In either case, it would automatically make the required entries in the database to maintain the link between the patient, sample, and the intermediate sample carriers.

A number of embodiments of the invention have been described. Nevertheless, it will be understood that various modifications may be made without departing from the spirit and scope of the invention. Accordingly, other embodiments are within the scope of the following claims.

What is claimed is:

1. A method for configuring a device controlling at least one instrument in a laboratory comprising:
    configuring said device to store at least one item of device information, wherein the at least one item of device information is input to or generated by the device;
    configuring said device to store at least one item of central information wherein at least one copy of the at least one item of central information is stored in at least one other device,
    wherein at least one of the items of central information and device information are used by said device in connection with processing performed by said at least one instrument;
    configuring said device to identify a carrier in said laboratory;
    receiving, by a label associated with said carrier, a signal from a label scanner; and
    transmitting, by said label in response to said signal from said label scanner, an electromagnetic response signal including a unique identifier for uniquely identifying said carrier in said laboratory.

2. The method of claim 1, wherein said device and said at least one other device communicate with a central server to maintain an up-to-date local copy of said at least one item of central information.

3. The method of claim 2, further comprising:
    configuring at least one item of device information as a new item of central information;
    communicating said new item of central information to said central server; and
    configuring said at least one other device in accordance with said new item of central information using said central server.

4. The method of claim 1, wherein said device, said at least one other device and said central server are included in a laboratory network.

5. The method of claim 4, wherein said central server is connected to a laboratory information system.

6. The method of claim 1, wherein said laboratory instrument is an anatomical pathology laboratory instrument.

7. The method of claim 4, wherein said device performs offline processing with respect to said at least one other device and said central server, and said device uses said at least one item of device information in said offline processing with said at least one instrument.

8. The method of claim 7, wherein said device synchronizes said at least one item of central information with said central server when said device completes said offline processing, said device and said at least one other device being configured to use different items of central information.

9. The method of claim 1, wherein said at least one item of central information includes the unique identifier and a protocol.

10. The method of claim 1, wherein said configuring said device to identify a carrier includes using a symbology used with optical encodings in the laboratory.

11. The method of claim 10, wherein one of said instruments controlled by said device operates in accordance with said symbology.

12. The method of claim 11, wherein an optical scanner is one of said instruments controlled by said device, said scanner supporting scanning operations in accordance with said symbology.

13. The method of claim 11, wherein a printer is one of said instruments controlled by said device, said printer supporting printing operations in accordance with said symbology.

14. The method of claim 11, wherein said label is a bar code label associated with said carrier, and said symbology is used with said bar code label in connection with processing within the laboratory.

15. The method of claim 14, wherein said bar code label encodes an identifier used to obtain data from a database about said carrier associated with said bar code label, said data including at least one of said items of central information and of device information.

16. The method of claim 1, wherein said electromagnetic response signal is produced using information encoded in said label associated with said carrier.

17. The method of claim 1, further comprising:
    determining a location of said carrier in said laboratory in accordance with said electromagnetic response signal.

18. The method of claim 1, wherein said label is affixed to a surface of said carrier.

19. The method of claim 1, wherein said label is embedded in said carrier.

20. The method of claim 19, wherein said label includes optically recognizable data which is readable by a machine.

21. The method of claim 1, further comprising:
    using said unique identifier to obtain additional information about said element from a database.

22. The method of claim 1, wherein said devices, a central server, and a laboratory information system are included in a laboratory network, said laboratory information system in communication with said central server, and said central server is in communication with said device.

23. A system for laboratory information management and control comprising:
    a laboratory information system having patient and laboratory information,
    a first device configured with an item of device information and configured to share an item of central information, said item of device information being input to or generated by the device, said device using at least one of said items of central information and of device information in connection with performing processing on at least one laboratory instrument connected to said first device;
    said first device being further configured to identify a carrier in said laboratory, receive, by a label associated with said carrier, a signal from a label scanner, and transmit, by said label in response to said signal from said label scanner, an electromagnetic response signal including a unique identifier for uniquely identifying said carrier in said laboratory;
    a second device configured to share said item of central information;
    at least one laboratory instrument controlled by said device; and
    a server in communication with said laboratory information system and said at least one device, said server managing a database including said item of central information, said server communicating with said first device and said second device to maintain a current copy of said item of central information in said database, and local copies of said item of central information at each of said devices.

* * * * *

UNITED STATES PATENT AND TRADEMARK OFFICE
CERTIFICATE OF CORRECTION

PATENT NO. : 9,659,153 B2  
APPLICATION NO. : 11/642253  
DATED : May 23, 2017  
INVENTOR(S) : Jose De La Torre-Bueno Page 1 of 1

It is certified that error appears in the above-identified patent and that said Letters Patent is hereby corrected as shown below:

In the Specification

In Column 1, Line 9, delete "Nov. 13, 2003" and insert -- Nov. 13, 2002 --, therefor.

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*